US006762555B1

(12) United States Patent
Kyushima et al.

(10) Patent No.: US 6,762,555 B1
(45) **Date of Patent: *Jul. 13, 2004**

(54) PHOTOMULTIPLIER TUBE AND RADIATION DETECTOR

(75) Inventors: Hiroyuki Kyushima, Hamamatsu (JP); Akira Atsumi, Hamamatsu (JP); Hideki Shimoi, Hamamatsu (JP); Tomoyuki Okada, Hamamatsu (JP); Masuo Ito, Hamamatsu (JP)

(73) Assignee: Hamamatsu Photonics K.K., Hamamatsu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/701,284

(22) PCT Filed: Jun. 1, 1999

(86) PCT No.: PCT/JP99/02922

§ 371 (c)(1), (2), (4) Date: Nov. 28, 2000

(87) PCT Pub. No.: WO99/63574

PCT Pub. Date: Dec. 9, 1999

(30) Foreign Application Priority Data

Jun. 1, 1998 (JP) .......................................... 10-151596
Jun. 1, 1998 (JP) .......................................... 10-151603

(51) Int. Cl.[7] ................................................ H01J 43/28
(52) U.S. Cl. ........................ 313/532; 313/544; 313/527
(58) Field of Search ................................ 313/528, 532, 313/541–544, 103 R, 103 CM, 105 R, 105 CM, 379, 384, 387; 250/207, 214 VT, 366

(56) References Cited

U.S. PATENT DOCUMENTS 2,416,376 A * 2/1947 Cawein ........................ 330/42
2,418,574 A * 4/1947 Cawein ........................ 330/42
4,221,967 A * 9/1980 Wang et al. ........... 250/363.02
4,426,596 A * 1/1984 Butterwick ................. 313/534
5,329,124 A 7/1994 Yamamoto et al.
5,504,386 A * 4/1996 Kyushima et al. ...... 313/103 R
5,594,301 A * 1/1997 Sawai et al. ................ 313/523
5,796,109 A * 8/1998 Frederick et al. ........... 250/368
6,472,664 B1 * 10/2002 Kyushima et al. .......... 250/366

FOREIGN PATENT DOCUMENTS

| EP | 66004 | 12/1982 |
|---|---|---|
| JP | 6295704 | 10/1994 |
| JP | 9001374 | 1/1997 |
| JP | A-9-320511 | 12/1997 |
| JP | A-10-214589 | 8/1998 |
| JP | A-10-241623 | 9/1998 |

* cited by examiner

*Primary Examiner*—Vip Patel
*Assistant Examiner*—Glenn Zimmerman
(74) *Attorney, Agent, or Firm*—Oliff & Berridge, PLC

(57) ABSTRACT

A photomultiplier tube has a side tube with a stem plate fixed on one end and a faceplate fixed on the other. The side tube is formed of metal, and at least the portion of the stem plate contacting the metal side tube is formed of metal. The side tube and stem plate are fused together by laser welding or electron beam welding to form an airtight vessel, such that the outer edge of the stem plate does not protrude further externally than the outer surface of the side tube.

13 Claims, 11 Drawing Sheets

PHOTOMULTIPLIER TUBE AND RADIATION DETECTOR

TECHNICAL FILED

The present invention relates to a photomultiplier tube designed to detect through multiplication weak light radiated onto a faceplate, and a manufacturing method thereof. The present invention also relates to a radiation detector using this type of photomultiplier tube.

BACKGROUND ART

Photomultiplier tubes are produced at various sizes to suit different uses. Conventional photomultiplier tubes are generally configured of a hermetically sealed vessel constructed entirely of glass. This type of photomultiplier tube has a substantially cylindrical glass side tube with a planar and substantially circular stem fitted on the bottom open end. A gas burner is applied to the area in which the periphery of the stem contacts the inner surface of the side tube, and the two are fused together by heat to form an airtight seal. A planar and substantially circular transparent faceplate is fused in the same manner to the top opening of the side tube, forming an airtight seal. A glass exhaust tube is provided in the stem, forming a fluid connection with the inside of the hermetically sealed vessel. After evacuating the vessel through the exhaust tube, an alkaline metal vapor is introduced into the vessel to form a photocathode on the inner surface of the faceplate and also to activate the secondary electron emitting surface of the electron multiplying section disposed inside the vessel.

As described above, the side tube and stem are fused together with heat from a gas burner in order to construct a photomultiplier tube having an airtight glass vessel. Further, after introducing the alkaline metal vapor, the exhaust tube is pinched off and sealed with the gas burner. Accordingly, it is necessary to prevent heat from damaging the electron multiplying section. Therefore, it has been necessary to maintain a distance of about 20–30 mm from the airtight fused junctions to the bottom of the electron multiplying section. Unfortunately, this inhibits downsizing of the photomultiplier tube.

While it depends on the application, the advantages of downsizing a photomultiplier tube are generally great. One example is a sanitation monitor that is used for detecting bacteria in restaurants and the like. The sanitation monitor employs a photomultiplier tube to detect light that is emitted from reactions between drugs and bacteria. Since this type of monitoring device should be portable and easy to use, the photomultiplier tubes used in the monitor must be small. A small enough photomultiplier tube can be mounted directly on a circuit board and treated in the same way as a resistor or capacitor, thereby making the tubes more convenient for device construction.

In light of these demands, small photomultiplier tubes having metal side tubes have been developed for practical uses in recent years. An example of this type of photomultiplier tube described in Japanese Unexamined Patent Application Publication Nos. HEI-5-290793 and HEI-9-306416 has a metal side tube having a polygonal cross-section with a flange portion protruding laterally from the bottom of the tube. Similarly, the metal stem plate is provided with a flange portion that protrudes laterally. The flange portions of the side tube and stem plate overlap and are fused through resistance welding to form a hermetically sealed vessel. Resistance welding is performed in such a way that current is applied to the joining parts, which are heated through the heat generated from resistance. When the parts reach an appropriate temperature, pressure is applied to weld them together. Hence, it is possible to avoid the thermal affects that resistance welding has on the electron multiplying section. As a result, the distance between the stem plate and electron multiplying section can be reduced, thereby achieving a smaller photomultiplier tube that is shorter in the axial direction.

With a photomultiplier tube of this construction, however, the flange portions required for resistance welding interfere with the use of the tube. For example, when photomultiplier tubes are used in gamma cameras and the like, in particular, it is necessary to arrange a plurality of photomultiplier tubes closely together and form a large area for receiving light. With this configuration, the flange portions contact other flange portions, forming dead spaces. Dead spaces are a hindrance to achieving a high-performance detecting device.

DISCLOSURE OF THE INVENTION

The present invention has been made to solve the above-described problems, and accordingly it is an object of the present invention to provide a photomultiplier tube and a method for manufacturing a smaller multiplier tube. It is another object of the present invention to provide a radiation detector with improved performance.

These objects will be attained by a method of manufacturing a photomultiplier tube having a faceplate, a photocathode for emitting electrons in response to light incident on the faceplate, an electron multiplying section for multiplying the electrons emitted from the photocathode, an anode for outputting an output signal based on the electrons multiplied by the electron multiplying section, a stem plate for fixedly supporting the electron multiplying section and the anode with stem pins, and a side tube with the stem plate fixed on one open end and the faceplate fixed on the other open end and enclosing the electron multiplying section and the anode, the method characterized by the steps of: providing a metal side tube formed of metal and a stem plate such that at least a portion contacting the metal side tube is formed of metal; aligning the metal side tube with the stem plate so that an outer edge of the stem plate does not protrude further externally than an outer surface of the metal side tube; and fusing the metal side tube to the stem plate at a point of contact between the metal side tube and the stem plate by laser welding or electron beam welding to form an airtight vessel.

The side tube is engaged with the stem plate such that only the outer side surface of the side tube or both the outer surface of the side tube and at least a portion of the outermost side edge of the stem plate are exposed on the outer surface of the airtight vessel, the parts being reshaped as necessary.

According to another aspect of the present invention, there is provided a photomultiplier tube including a faceplate, a photocathode for emitting electrons in response to light incident on the faceplate, an electron multiplying section, disposed inside an airtight vessel, for multiplying the electrons emitted from the photocathode, and an anode for outputting an output signal based on the electrons multiplied by the electron multiplying section, characterized in that the airtight vessel comprises:

a stem plate for fixedly supporting the electron multiplying section and the anode with stem pins;

a metal side tube with the stem plate fixed on one open end, and enclosing the electron multiplying section and the anode; and a faceplate fixed on the other open end of the metal side tube, wherein the stem plate is welded on the one open end of the metal side tube, a top surface of the stem plate contacting a bottom end of the metal side tube such that an outer surface of the metal side tube is flush with an edge surface of the stem plate, at least a portion of the top surface of the stem plate in contact with the metal side tube being formed of metal.

Welding the side tube to the stem plate such that the outer surface of the side tube is flush with the edge surface of the stem plate eliminates the flange-like protrusions on the bottom of the photomultiplier tube. While posing difficulties for resistance welding, this construction allows the external dimensions of the photomultiplier tube to be reduced and enables the side tubes to be positioned adjacent one another when justaposing a plurality of photomultiplier tubes. Accordingly, employing a welding method to join the metal stem plate and side tube enables the photomultiplier tubes to be more densely packed together.

A cutout portion may be provided in the top surface on the edge of the stem plate for supporting the bottom end of the side tube. Hence, the side tube can be placed stably on the stem plate and easily position the side tube in relation to the stem plate before welding the two together. Moreover, the reinforced construction can oppose a force toward the inside of the vessel 5A attempting to bend the side tube 2.

It is preferable that the side tube be fusion welded to the stem plate. In contrast to resistance welding, a fusion welding method does not require that pressure be added to the portions of the side tube and stem plate that are being joined. Accordingly, residual stress that can lead to cracking during operations is not generated at this junction, thereby greatly improving durability of the apparatus.

As the fusion welding, laser welding or electron beam welding is preferable. The methods of laser welding and electron beam welding generate little heat at the junction. Therefore, the glass tablets fixing the stem pins to the stem plate are not apt to crack from the effects of the heat when the stem pins are near the side tube. Accordingly, it is possible to move these stem pins closer to the side tube and expand the electron multiplying section laterally, creating a greater electron receiving surface area in the electron multiplying section.

The entire stem plate can be formed of metal, or a metal stem support member in contact with the lower end of the side tube extending substantially in the axial direction of the same, and a glass stem plate.

According to another aspect of the present invention, there is provided a radiation detector including a scintillator for emitting fluorescent light in response to radiation generated from an object of analysis, a plurality of photomultiplier tubes, each having a faceplate disposed in opposition to the scintillator, for outputting electric charges based on fluorescent light emitted from the scintillator, and a position calculating section for performing calculations on the electric charges output from the plurality of photomultiplier tubes and outputting positioning signals of radiation issued in the object of analysis. The photomultiplier tube used in this radiation detector includes a photocathode for emitting electrons in response to light incident on the faceplate; an electron multiplying section, disposed inside an airtight vessel, for multiplying the electrons emitted from the photocathode; and an anode for outputting an output signal based on the electrons multiplied by the electron multiplying section. The airtight vessel comprises:

a metal stem plate for fixedly supporting the electron multiplying section and the anode with stem pins;

a metal side tube with the metal stem plate fixed on one open end, and enclosing the electron multiplying section and the anode, wherein the metal stem plate is fixed by welding to the metal side tube such that an outermost edge of the metal stem plate does not protrude outward from an outer surface of the metal side tube: and the faceplate fixed on the other open end of the metal side tube.

Joining the side tube and stem plate through a welding process in the photomultiplier tubes used in this type of radiation detector, such that the outer surface of the metal side tube is flush with the edge surface of the stem plate, eliminates the flange-like protrusion from the bottom of the photomultiplier tube. Accordingly, although resistance welding is not appropriate for this construction, the dimensions of the photomultiplier tube can be reduced and the side tubes can be arranged in close contact with one another when employing a plurality of juxtaposed photomultiplier tubes. Accordingly, when the photomultiplier tubes are arranged in order that the faceplates confront the scintillator, the tubes can be densely packed, thereby easily securing a light receiving area with an extremely small amount of dead space, which forms non-sensitive areas. This configuration contributes to further improved performance of the radiation detector.

BEST MODE FOR CARRYING OUT THE INVENTION

A photomultiplier tube according to preferred embodiments of the present invention will be described while referring to the accompanying drawings.

Figure 1:
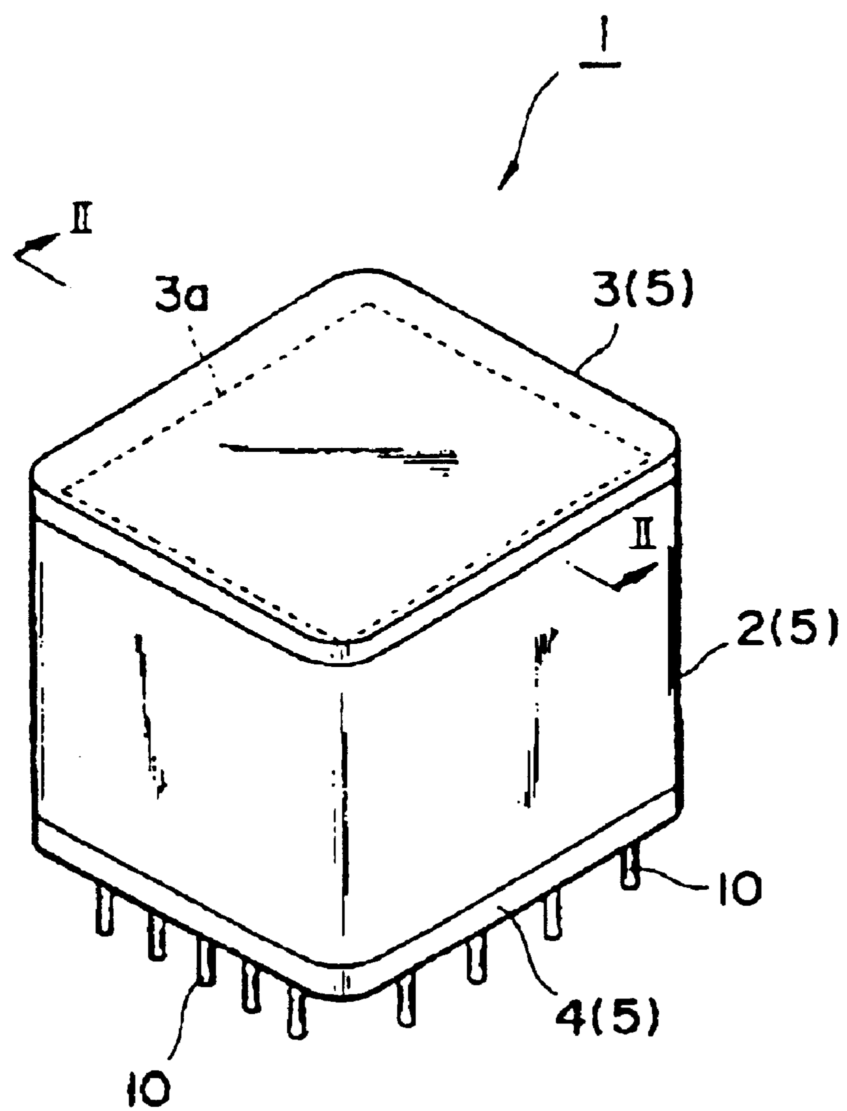
FIG. 1 is a perspective view showing a photomultiplier tube according to a first embodiment of the present invention.
Figure 2:
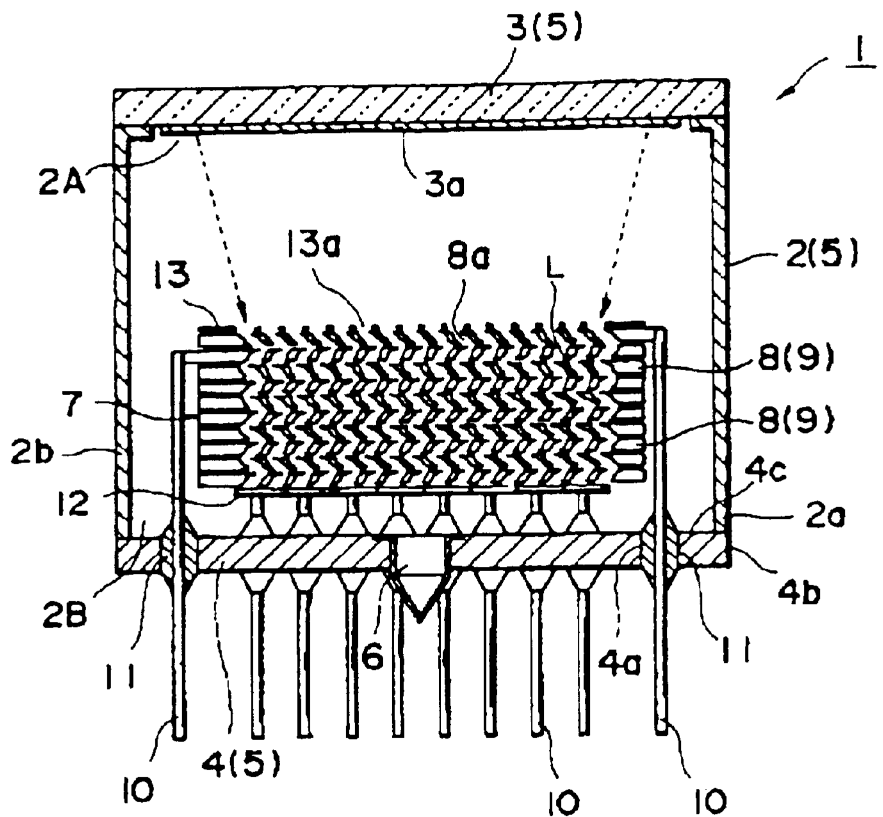
FIG. 2 is a cross-sectional view of the photomultiplier tube along the plane indicated by the arrows II in FIG. 1.

FIG. 1 is a perspective view showing a photomultiplier tube according to the first embodiment. FIG. 2 is a cross-sectional view of the photomultiplier tube in FIG. 1. A photomultiplier tube 1 shown in these figures includes a side tube 2 formed of a metallic material such as Kovar metal or stainless steel and shaped substantially like an angular cylinder and having an open end 2A on one end and an open end 2B on the other; a faceplate 3 formed of glass material that is fused to the open end 2A; and a stem plate 4 formed of a metal (such as Kovar metal or stainless steel) is fused to the open end 2B. A photocathode 3*a* is formed on the inner surface of the faceplate 3 for converting light into electrons. The photocathode 3*a* is formed by causing alkaline metal vapor to react to antimony that has been pre-deposited on the faceplate 3. Here, the side tube 2, faceplate 3, and stem plate 4 are the components that construct an airtight vessel 5.

A metal exhaust tube 6 is fixed in the center of the stem plate 4. After operations for assembling the photomultiplier tube 1 are completed, the exhaust tube 6 is used to evacuate the vessel 5 using a vacuum pump (not shown) and to introduce an alkaline metal vapor into the vessel 5 when forming the photocathode 3*a*.

A block-shaped layered electron multiplier 7 is disposed inside the vessel 5. The electron multiplier 7 includes a ten-stage electron multiplying section 9 that has ten plate-shaped dynodes 8 constructed in layers. The electron multiplier 7 is supported in the vessel 5 by a plurality of stem pins 10 formed of Kovar metal. The stem pins 10 penetrate the stem plate 4. Internal ends of each stem pin 10 connect electrically to each dynode 8. Pinholes 4*a* are formed in the stem plate 4 to allow each stem pin 10 to pass through. A tablet 11 made of Kovar glass fills each pinhole 4*a* to form a hermetic seal between each stem pin 10 and the stem plate 4. Each stem pin 10 is fixed to the stem plate 4 via the tablet 11. The stem pins 10 are arranged in a ring around the stem plate 4 near an edge surface 4*b* of the stem plate 4.

An insulation substrate (not shown) is disposed in the electron multiplier 7 at a position below the electron multiplying section 9. Anodes 12 are juxtaposed on top of this insulation substrate. A flat focusing electrode plate 13 is disposed on the top layer of the electron multiplier 7 between the photocathode 3*a* and the electron multiplying section 9 and is formed with a plurality of slits 13*a* that are arranged linearly in the same direction. Each dynode 8 in the electron multiplying section 9 is also formed with a plurality of slits 8*a* having the same number as the slits 13*a* and also arranged linearly in a single direction.

Each electron multiplying path L that is formed by the slits 8*a* and pass through all layers of the dynodes 8 is given a one-on-one correspondence to each slit 13*a* in the focusing electrode plate 13, thereby forming a plurality of linear channels in the electron multiplier 7. Each anode 12 that is provided in the electron multiplier 7 has a one-on-one correspondence to each channel. By connecting each anode 12 to each stem pin 10, it is possible to extract discrete output from the vessel 5 via each stem pin 10.

In this way, linear channels are formed in the electron multiplier 7. A prescribed voltage is supplied to the electron multiplying section 9 and the anode 12 by connecting the stem pins 10 to a bleeder circuit. The photocathode 3*a* and focusing electrode plate 13 are set to the same potential, while the dynodes 8 and anode 12 are set to increasingly higher potentials beginning from the top stage. Light striking the faceplate 3 is converted to electrons by the photocathode 3*a*. The electrons enter prescribed channels by the electron lens effect of the focusing electrode plate 13. While passing through the electron multiplying path L of the dynodes 8, the electrons multiply at each stage of the dynodes 8, impinging on the anode 12. As a result, the output from each channel can be obtained from each anode.

Next, a method of connecting the metal stem plate 4 to the side tube 2 formed of the same metal will be described.

Figure 3:
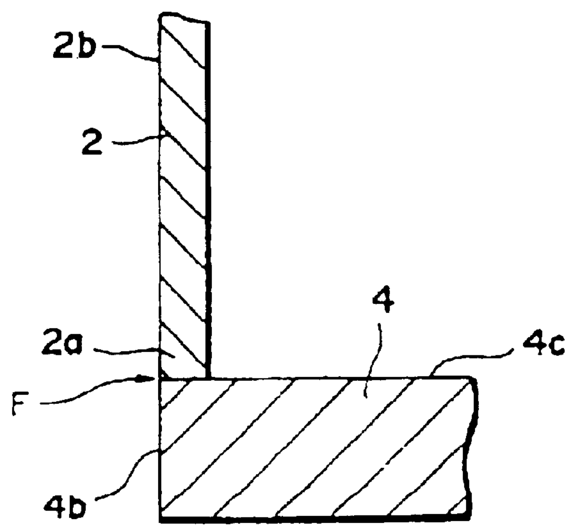
FIG. 3 is an enlarged cross-sectional view of the relevant part in FIG. 2.

According to the first embodiment of the present invention shown in FIG. 3, a bottom end 2*a* of the side tube 2 extending substantially in the axial direction of the tube is placed in contact with a top surface 4*c* of the stem plate 4, such that an outer surface 2*b* of the side tube 2 is flush with the edge surface 4*b* of the stem plate 4 along the axial direction. This construction eliminates protrusions such as a flange at the bottom of the photomultiplier tube 1. Referring to the point at which the bottom end 2*a* contacts the top surface 4*c* as a junction F, a laser beam external to the vessel 5 is irradiated directly horizontal and/or at a prescribed angle to the junction F, welding the two components together.

Next, other preferred embodiments of the present invention will be described regarding the junction between the stem plate 4 and the side tube 2. The basic construction and appearance of the photomultiplier tube in the various embodiments described below are substantially the same as that in the first embodiment. Therefore, like parts and components are designated by the same reference numerals to avoid duplicating description.

Figure 4:
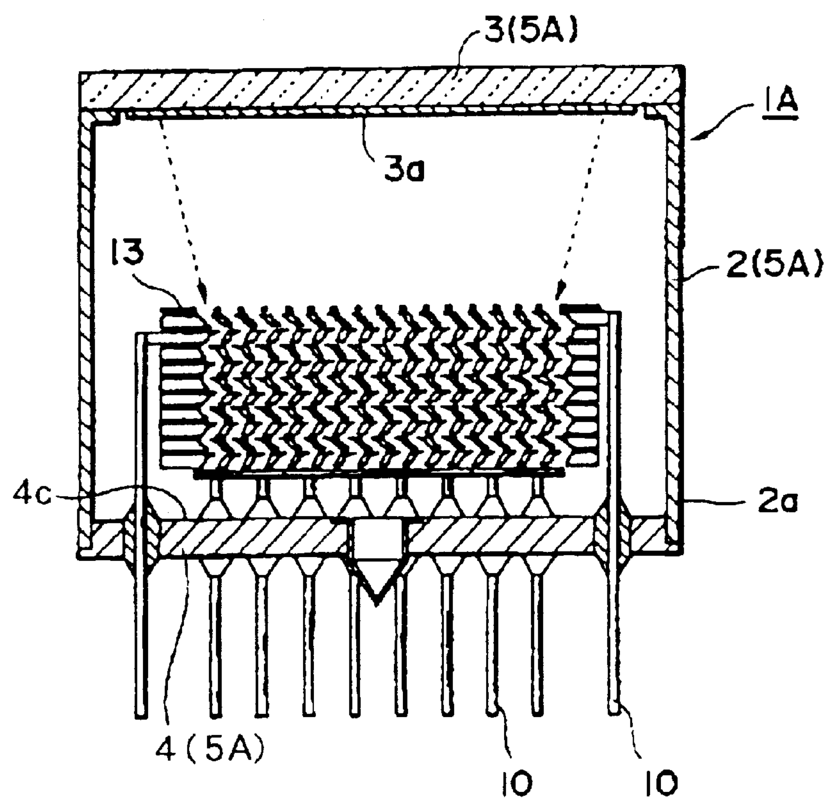
FIG. 4 is a cross-sectional view showing a photomultiplier tube according to a second embodiment.
Figure 5:
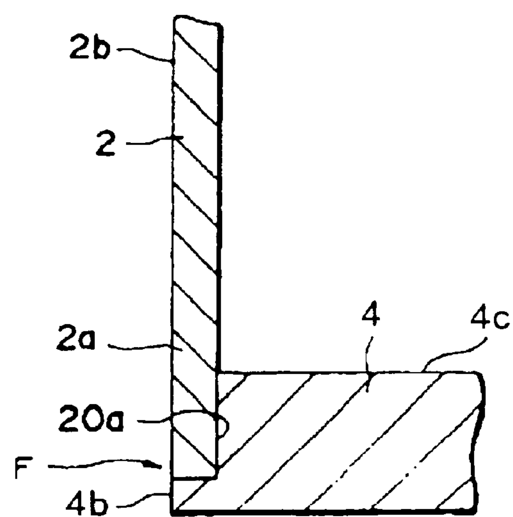
FIG. 5 is an enlarged cross-sectional view of the relevant part in FIG. 4.

FIGS. 4 and 5 show a photomultiplier tube according to a second embodiment of the present invention.

As shown in the drawings, a photomultiplier tube 1A has the metal stem plate 4. A cutout portion 20*a* is formed in the outer edge of the top surface 4*c* and has a step shape for placing the bottom end 2*a* of the side tube 2. The cutout portion 20*a* is formed in the top surface 4*c* around the entire edge of the stem plate 4 and has a rectangular ring shape that conforms to the shape of the side tube 2. The bottom end of the side tube 2 fits into the cutout portion 20*a*. The outer surface 2*b* is flush in the axial direction with the edge surface 4*b*.

By employing the fitting construction of the side tube 2 described above, the side tube 2 can be placed stably on the stem plate 4 before welding the junction F. Further, this construction facilitates positioning the side tube 2 over the stem plate 4. Moreover, after the junction F is welded, the reinforced construction can oppose a force toward the inside of the vessel 5A attempting to bend the side tube 2.

A laser beam external to the vessel 5A is irradiated directly horizontal to the junction F and/or at a prescribed angle to weld the components together. It is also possible to weld the junction F with an electron beam instead of the laser beam. In either case, the beams will not enter the vessel 5A during the welding process. Hence, the effects of heat on the internal parts can be avoided, as the formation of the side tube 2 prevents the beam from entering.

Figure 6:
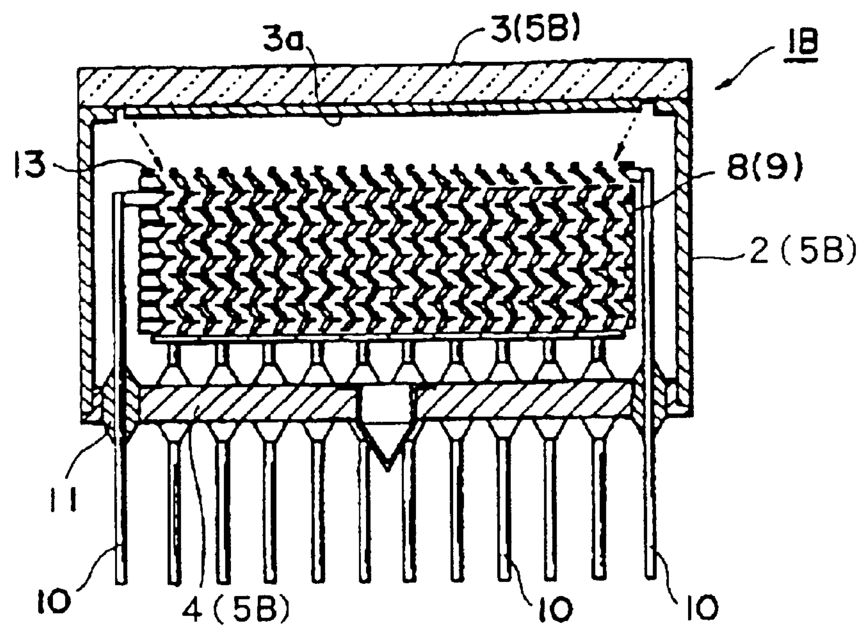
FIG. 6 is a cross-sectional view showing a photomultiplier tube according to a third embodiment.
Figure 7:
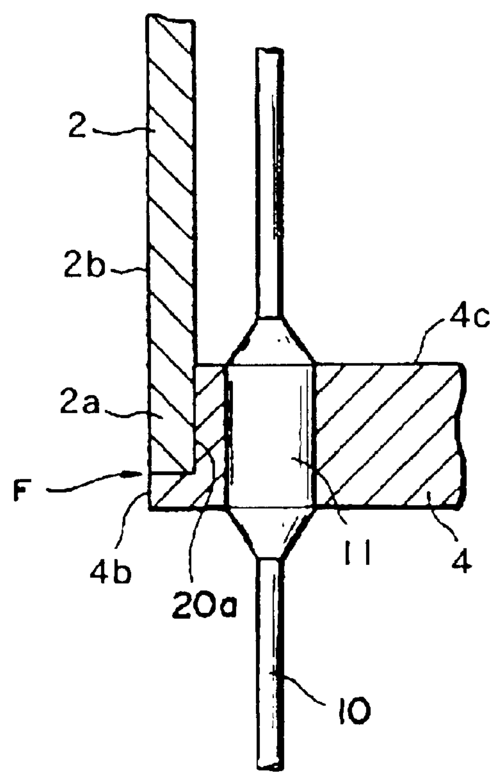
FIG. 7 is an enlarged cross-sectional view of the relevant part in FIG. 6.

FIGS. 6 and 7 show a photomultiplier tube 1B according to a third embodiment of the present invention.

In the photomultiplier tube 1B shown in FIG. 6, laser welding is employed to fuse the side tube 2 and stem plate 4 together, decreasing the amount of heat generated at the junction F. As a result, the stem pins 10 can be disposed near the side tube 2, as shown in FIG. 7, when the bottom end 2*a* is fit into the cutout portion 20*a*, such that the outer surface 2*b* and edge surface 4*b* are flush. This construction substantially prevents the effects of heat from generating cracks in the glass tablet 11 fixing the stem pins 10 to the stem plate 4. Accordingly, the stem pins 10 can be placed closer to the side tube 2, enabling the dynodes 8 to be expanded laterally. Such expansion Increases the number of channels that can be formed in the electron multiplying section 9, providing a larger effective area in the electron multiplying section 9. By increasing the effective surface area in the electron multiplying section 9, it is possible to position the electron multiplying section 9 closer to the photocathode 3*a*, since the photoelectrons emitted from the photocathode 3*a* toward the focusing electrode plate 13 do not move at a large angle. This construction enables the height dimension of the vessel 5B to be reduced, thereby forming a compact photomultiplier tube having a larger effective surface area.

With conventional resistance welding, a distance of approximately 3.5 mm must be formed between the edge of the stem plate 4 and the center of the stem pins 10. Using laser beam or electron beam welding, however, it has been confirmed that a distance of 1.1 mm is sufficient. While the distance from the photocathode 3*a* to the focusing electrode plate 13 in the photomultiplier tube 1A of FIG. 4 is 7 mm, the lateral expansion of the electron multiplying section 9 in the photomultiplier tube 1B of FIG. 6 enables this distance to be reduced to 2.5 mm. By employing the laser beam or electron beam welding method, it is not only possible to eliminate the flange from the photomultiplier tube, but also to reduce the height dimension, thereby making great advances toward producing a compact photomultiplier tube.

When densely juxtaposing a plurality of photomultiplier tubes, the existence of a flange on the outside of the photomultiplier tubes has a great effect on this arrangement, particularly as the external dimensions decrease. For example, if an angular side tube 2 has external side dimensions of 25 mm and if the flange used for resistance welding has a width of 2 mm and protrudes externally around the entire edge of the tube, the flange portion occupies nearly 20 percent of the dimensions of the tube. Arranging this type of photomultiplier tube in a dense formation would generate a large proportion of dead space.

Figure 8:
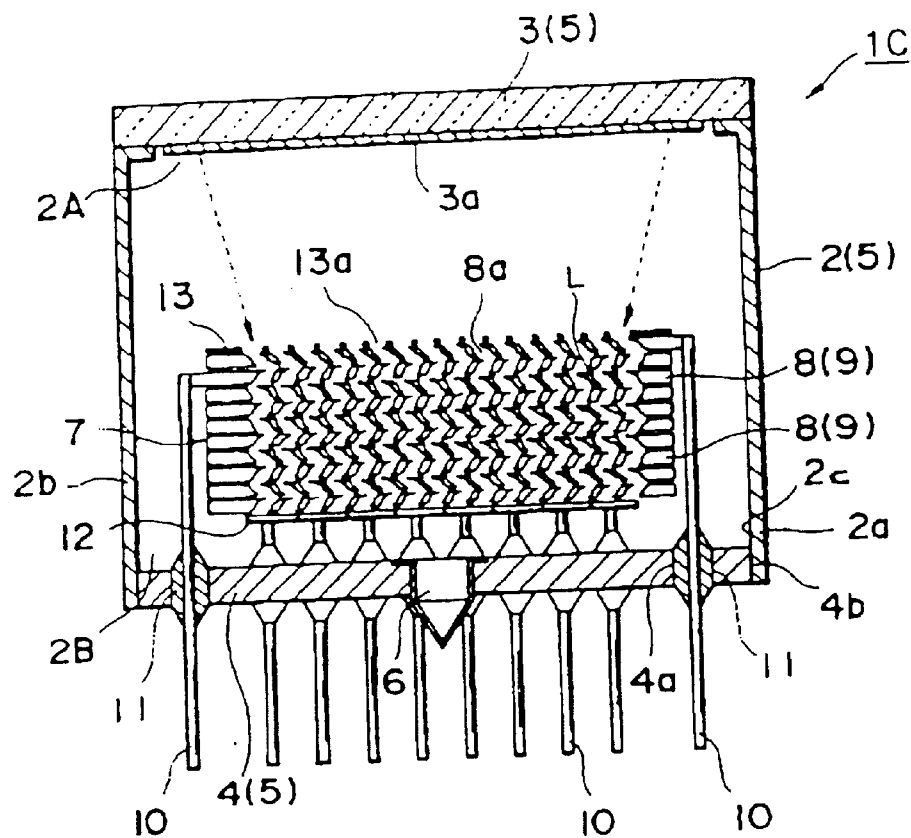
FIG. 8 is a cross-sectional view showing a photomultiplier tube according to a fourth embodiment.
Figure 9:
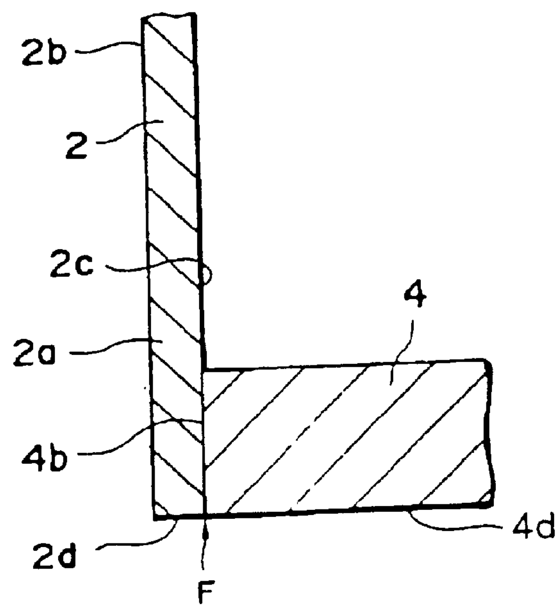
FIG. 9 is an enlarged cross-sectional view of the relevant part in FIG. 8.

FIGS. 8 and 9 show a photomultiplier tube according to a fourth embodiment of the present invention.

When forming an airtight weld between the stem plate 4 and side tube 2 shown in FIG. 9, the stem plate 4 is inserted into the open end 2B of the side tube 2, such that an inner surface 2*c* on the bottom end 2*a* contacts the edge surface 4*b*. At this time, a bottom surface 4*d* of the stem plate 4 is flush with a bottom end surface 2*d* of the side tube 2 in order that the bottom end surface 2*d* does not protrude lower than the stem plate 4. Accordingly, the outer surface 2*b* along the bottom end 2*a* extends substantially in the axial direction, and the flange protrusion is eliminated from the bottom end of the photomultiplier tube 1C. When welding the junction F, a laser beam external to the photomultiplier tube 1C is radiated from directly beneath the junction F. Eliminating a flange-like protrusion from the bottom of the photomultiplier tube 1C poses difficulties for resistance welding. However, this construction allows the external dimensions of the photomultiplier tube 1C to be reduced and helps to eliminate as much dead space as possible when justaposing a plurality of photomultiplier tube 1C, by enabling the side tubes 2 to be positioned close to one another. Accordingly, employing a laser welding method to join the stem plate 4 and side tube 2 can help reduce the size of the photomultiplier tube 1C and enables such photomultiplier tube 1C to be more densely packed together.

Figure 10:
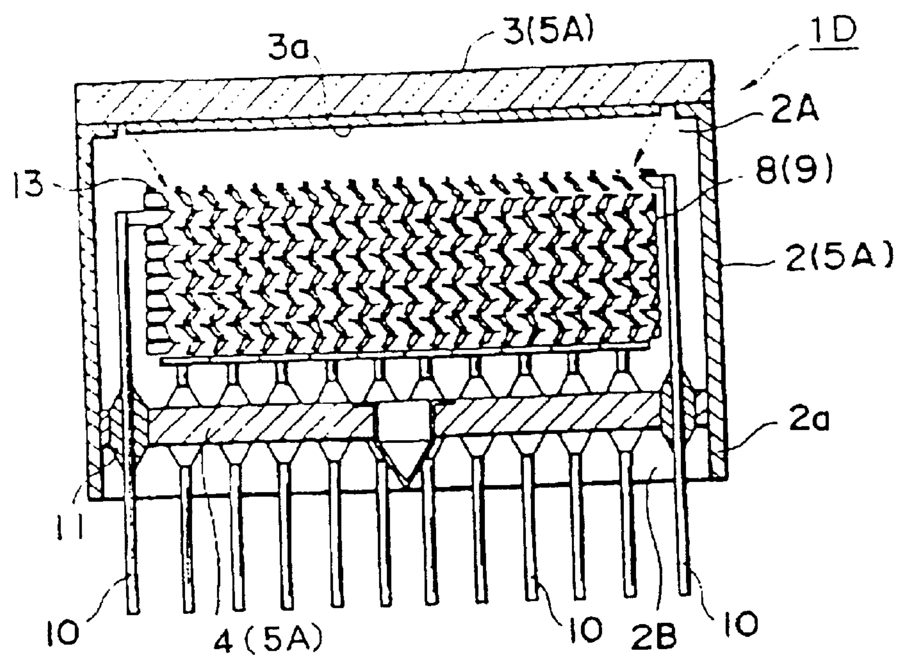
FIG. 10 is a cross-sectional view showing a photomultiplier tube according to a fifth embodiment.
Figure 11:
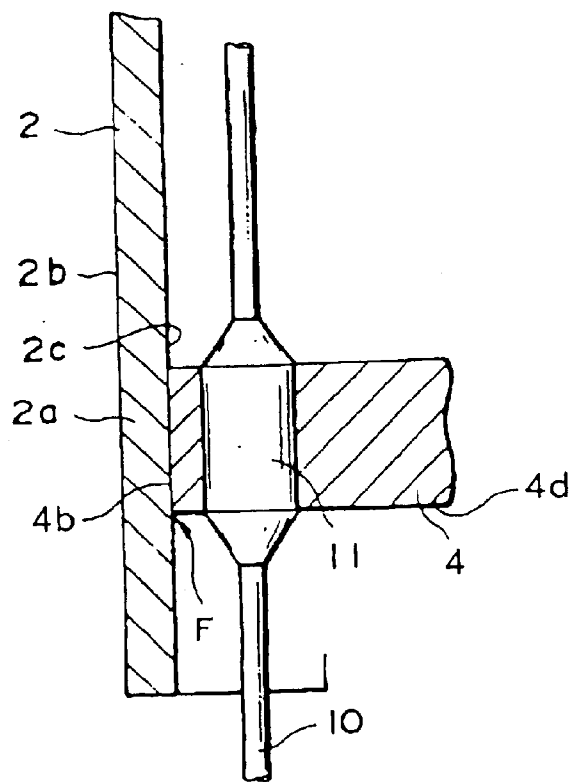
FIG. 11 is an enlarged cross-sectional view of the relevant part in FIG. 10.

FIGS. 10 and 11 show a photomultiplier tube according to a fifth embodiment of the present invention.

As shown in FIGS. 10 and 11, a photomultiplier tube 1D is formed such that the bottom end 2*a* has a free end extending in the axial direction. Hence, the stem plate 4 is inserted through the open end 2B, such that the edge surface 4*b* contacts and slides inwardly on the inner surface 2*c* of the bottom end 2*a*. With this configuration, the distance between the top layer of the dynodes 8 in the electron multiplying section 9, which is fixed to the stem plate 4, and the photocathode 3*a* can easily be adjusted before the welding process to suit the need. This is performed simply by pushing on the bottom surface 4*d* of the stem plate 4 toward the inside of the side tube 2. Although the side tube 2 in the photomultiplier tube 1D shown in FIG. 10 extends in the axial direction of the tube, the side tube 2 can also be formed such that the open end 2B is wider than the open end 2A to facilitate insertion of the stem plate 4 into the photomultiplier tube 1D.

When employing laser welding to weld the junction F, it is possible to decrease the heat generated at the junction F. Hence, as described in the third embodiment shown in FIGS. 6 and 7, the stem pins 10 can be positioned closer to the side tube 2, thereby producing a more compact photomultiplier tube of the same size described in the third embodiment.

Figure 12:
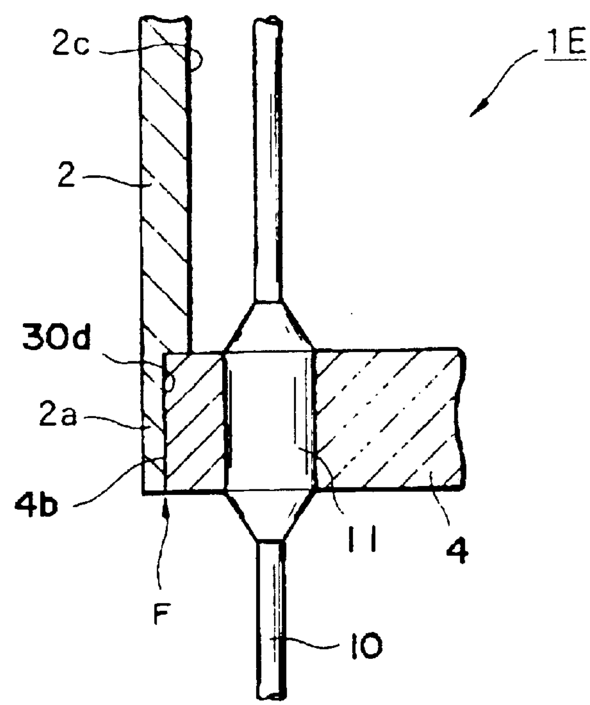
FIG. 12 is a cross-sectional view showing the relevant part of a photomultiplier tube according to a sixth embodiment.

FIG. 12 shows a photomultiplier tube according to the sixth embodiment of the present invention.

In a photomultiplier tube 1E of the sixth embodiment, a cutout portion 30*d* having a cross section shaped as the letter L is formed in the inner surface 2*c*. The cutout portion 30*d* enables the outer edge of the stem plate 4 to be inserted therein. The cutout portion 30*d* forms a rectangular ring around the entire inner surface 2*c* and conforms to the outer shape of the stem plate 4. By employing this construction, it is possible to rest the side tube 2 stably on the stem plate 4 before welding the junction F, thereby easily positioning the side tube 2 in relation to the stem plate 4. Moreover, the interval between the top layer of the dynodes 8 in the electron multiplying section 9, which is fixed to the stem plate 4, and the photocathode 3*a* formed on the faceplate 3 can be easily set by adjusting the depth of the cutout portion 30*d*.

The junction F is welded by irradiating a laser beam thereon. It is also possible to use an electron beam in place of the laser beam. In either case, the beam does not enter the evacuated vessel during the welding process, thereby avoiding heat affecting the internal components, since the cutout portion 30*d* blocks the penetration of such beams.

Figure 13:
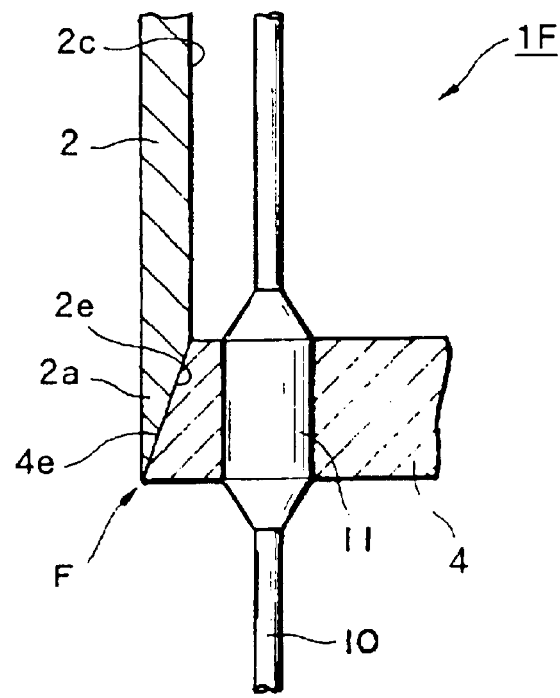
FIG. 13 is a cross-sectional view showing the relevant part of a photomultiplier tube according to a seventh embodiment.

FIG. 13 shows a photomultiplier tube according to the seventh embodiment of the present invention.

In a photomultiplier tube 1F of the seventh embodiment, a tapered surface 2*e* is formed in the inner surface 2*c* of the bottom end 2*a* and a tapered edged surface 4*e* is formed in the stem plate 4. The tapered surface 2*e* forms a rectangular ring around the entire inner surface 2*c* and conforms to the tapered edged surface 4*e* of the stem plate 4. By employing this construction, it is possible to rest the side tube 2 stably on the stem plate 4 before welding the junction F, thereby easily positioning the side tube 2 in relation to the stem plate 4.

Figure 14:
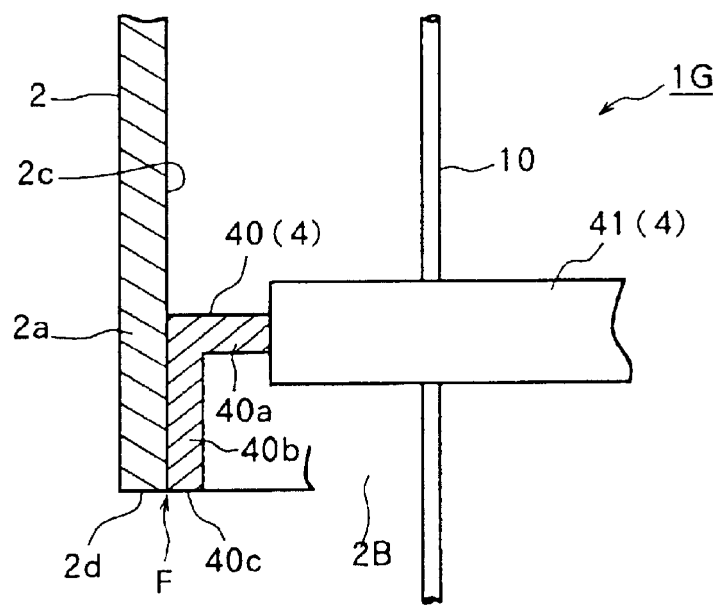
FIG. 14 is a cross-sectional view showing the relevant part of a photomultiplier tube according to an eighth embodiment.

FIG. 14 shows a photomultiplier tube according to the eighth emodiment of the present invention.

A photomultiplier tube 1G of the eighth embodiment includes a metal stem support member 40 that contacts the inner surface 2*c* of the bottom end 2*a*; and a glass stem plate 41 that is square-shaped and planar and supported by this stem support member 40. The stem support member 40 has a cross-section substantially shaped like the letter L having a horizontal portion 40*a* and a vertical portion 40*b*. The horizontal portion 40*a* is fixed to each side surface of the stem plate 41. The vertical portion 40*b* extends in the axial direction of the tube while contacting the inner surface 2*c*. A bottom end surface 40*c* of the vertical portion 40*b* is flush with the outer surface 2*b*. The stem pins 10 penetrate the stem plate 41. In the first to seventh embodiments, the tablets 11 formed of Kovar glass fill each pinhole 4*a* through which the stem pins 10 penetrate, in order to maintain insulation between the stem pins 10 and the metal stem plate 4. In the present embodiment, however, the tablets 11 are unnecessary because the stem pins 10 penetrate a glass stem plate 41, which is formed of glass.

In order to manufacture the photomultiplier tube 1G of the present embodiment, the stem support member 40 is prefixed to all sides of the stem plate 41, thereby forming the stem plate 4. The stem plate 4 is inserted into the side tube 2 through the open end 2B, sliding the edge surface 4*b* in contact with the inner surface 2*c*. The stem plate 4 is slid into the side tube 2 until the bottom end surface 40*c* is flush with the bottom end surface 2*d*. The junction F is welded by a laser.

In the present embodiment, the interval between the top layer of the dynodes 8 in the electron multiplying section 9, which is fixed to the stem plate 4, and the photocathode 3*a* formed on the faceplate 3 can be regulated by adjusting the length of the vertical portion 40*b*.

Figure 15:
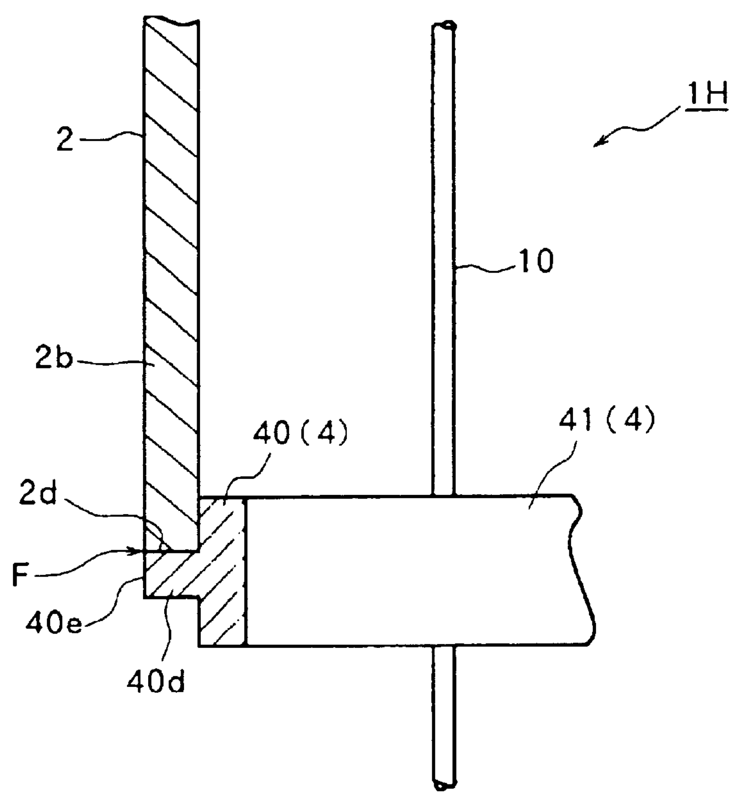
FIG. 15 is a cross-sectional view showing the relevant part of a photomultiplier tube according to a ninth embodiment.

FIG. 15 shows a photomultiplier tube according to a eighth embodiment of the present invention. Similar to the ninth embodiment shown in FIG. 14, a photomultiplier tube 1H shown in FIG. 15 includes the stem plate 4 configured of the stem support member 40 and the stem plate 41, wherein the stem plate 4 is welded to the bottom end 2*a* to form an airtight seal. The stem support member 40 has a cross section shaped substantially like the letter T. The top surface of a horizontal protrusion 40*d* of the stem support member 40 contacts the bottom end surface 2*d* of the side tube 2, such that an edge surface 40*e* of the horizontal protrusion 40*d* is flush with the outer surface 2*b* in the axial direction of the side tube 2.

The horizontal protrusion 40*d* of the stem support member 40 is preprocessed to have a protruding length equivalent to the thickness of the side tube 2. With this configuration, it is possible to mount the side tube 2 stably on the stem plate 4 prior to laser welding the junction F, facilitating the positioning of the side tube 2.

The photomultipliers tubes in all the embodiments described above are constructed without a flange-like protrusion. As a result, it is difficult to join the stem plate 4 and side tube 2 using resistance welding method that is employed in the conventional method. However, the junction can be joined through laser welding. As a result, the present invention can reduced the dimensions of the photomultiplier tube, thereby eliminating as much dead space as possible when a plurality of photomultiplier tubes are arranged together, enabling the side tubes 2 to be disposed near one another. Hence, the use of laser welding to join the stem plate 4 and side 2 can reduce the size of the photomultiplier tube and enable more densely packed arrays.

Further, the use of a laser for welding the side tube 2 to the stem plate 4 differs from resistance welding by eliminating the need to apply pressure on the side tube 2 and the stem plate 4 at the junction F. Accordingly, residual stress is not generated at the junction F. This makes it unlikely for cracking to occur during use at the junctions and greatly helps improve the durability of the apparatus and strengthens the hermetic seal.

In the embodiments described above, laser welding was used as the example for welding the side tube 2 and the stem plate 4 together. However, it is also possible to use an electron beam in place of the laser beam. Since both laser beam and electron beam welding can reduce the amount of heat generated at the junction F compared to that generated during resistance welding, the effects of heat on components mounted in the vessel 5 is extremely small when assembling the photomultiplier tube.

Next, the example of a radiation detector employing a plurality of photomultiplier tubes densely packed together will be described. For convenience sake, the photomultiplier tube 1 shown in FIG. 1 will be used in the description, although the same radiation detector can be constructed using a photomultiplier tube described in any of the embodiments above.

Figure 16:
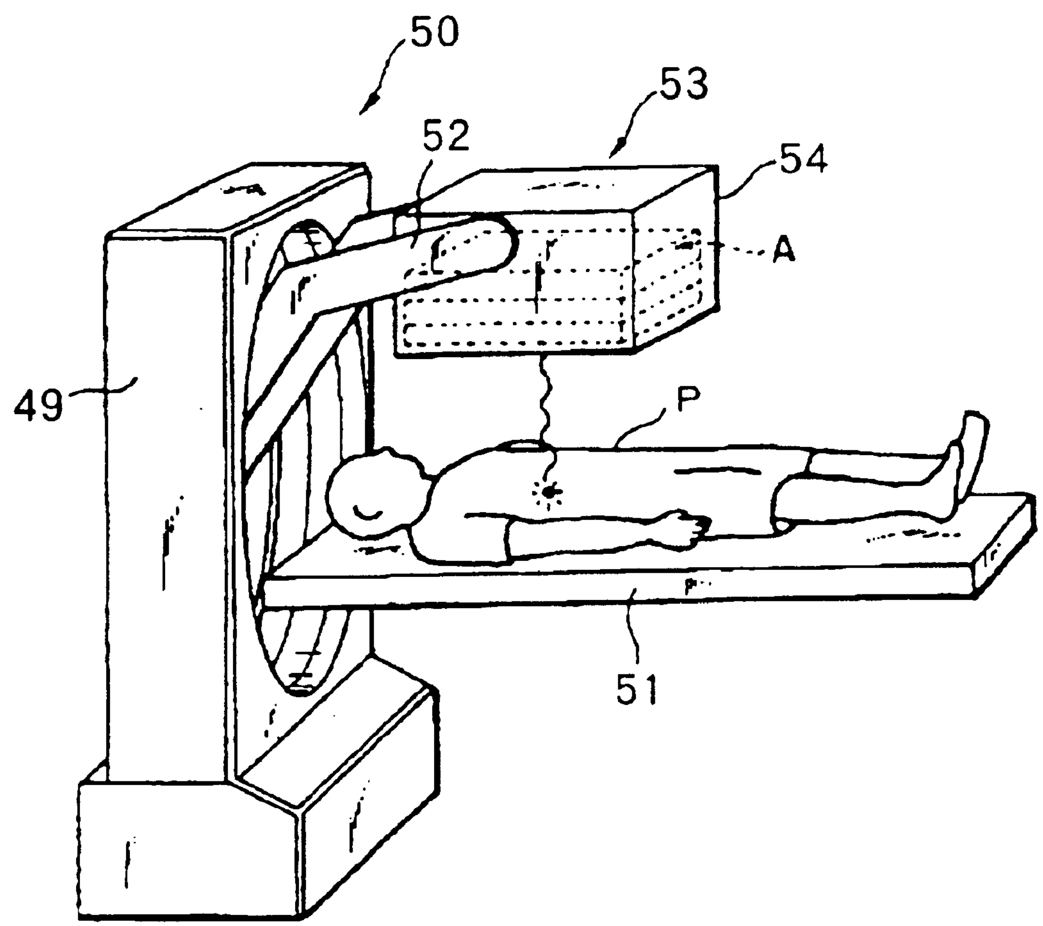
FIG. 16 is a perspective view showing a type of radiation detector employing the photomultiplier tube according to the present invention.

As shown in FIG. 16, a gamma camera 50 serves as the radiation detector of the present example. The gamma camera 50 was developed in nuclear medicine as a diagnostic apparatus. The gamma camera 50 includes a support frame 49; arms 52 extending from the support frame 49; a detector 53 supported by the arms 52; and a bed 51 positioned directly underneath the detector 53 for supporting a prostrated patient to be examined.

Figure 17:
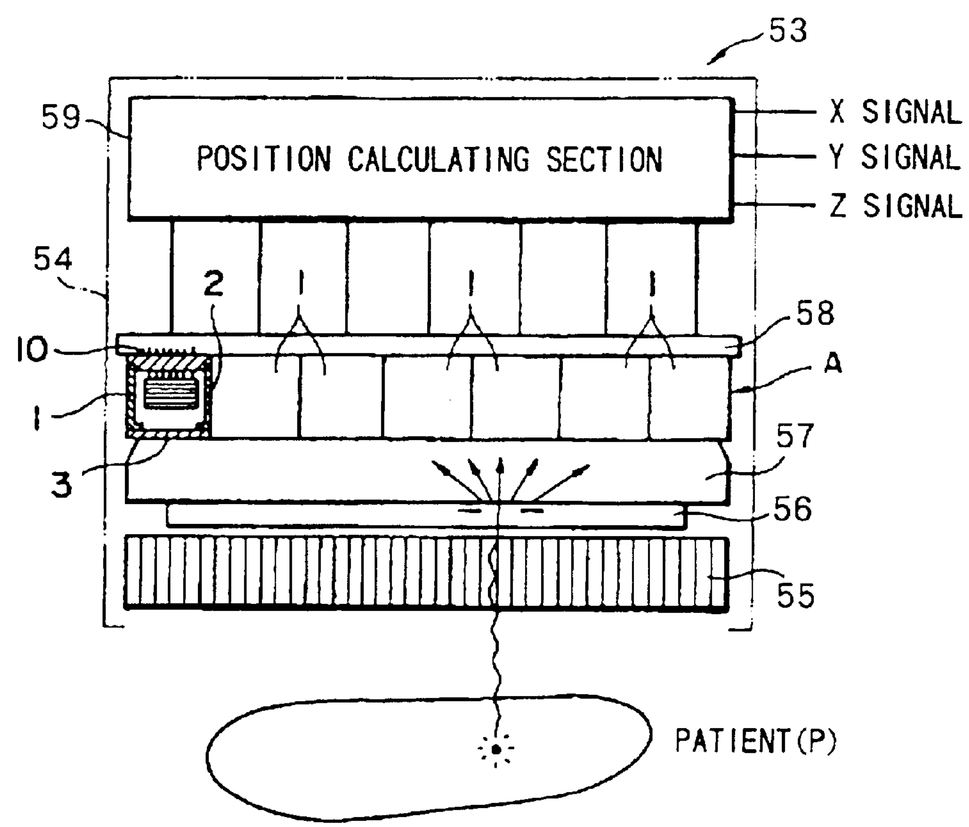
FIG. 17 is a side view showing the internal structure of the radiation detector of FIG. 16.

As shown in FIG. 17, the detector 53 includes an outer casing 54; a collimator 55 provided at the bottom level of the outer casing 54 at a position opposing the diseased part of the patient; a scintillator 56 disposed above the collimator 55 in the outer casing 54; a group of photomultiplier tubes A; and a light guide 57 for fixing the scintillator 56 to the group of photomultiplier tubes A. The group of photomultiplier tubes A includes a plurality of the photomultiplier tubes 1 juxtaposed. The faceplates 3 of the photomultiplier tubes 1 face downward in opposition to the scintillator 56 since the scintillator 56 emit fluorescent light onto the faceplate 3 via the light guide 57.

Figure 18:
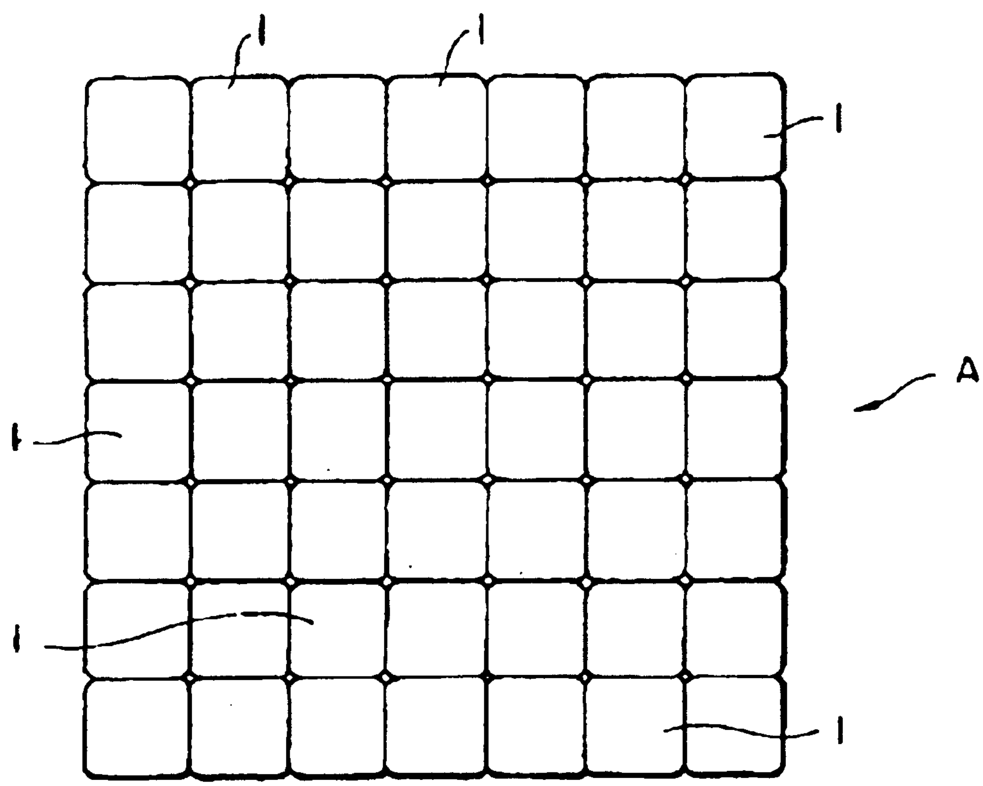
FIG. 18 is a plan view showing the photomultiplier tubes of FIG. 1 arranged in a matrix formation.

When using the plate-shaped scintillator 56, the group of photomultiplier tubes A is arranged in a densely packed matrix formation, as shown in FIG. 18, wherein the side tubes 2 of the photomultiplier tubes 1 are in close contact with one another. The matrix formation of the group of photomultiplier tubes A is achieved by inserting and fixing the stem pins 10 of each photomultiplier tube 1 into a socket member 58. In addition, a position calculating section 59 for computing processes based on charges output from each stem pin 10 of each photomultiplier tube 1 is provided in the outer casing 54. The position calculating section 59 outputs an X signal, Y signal, and Z signal for creating a 3-dimensional image on a display monitor (not shown). The light guide 57 converts gamma rays generated from the diseased part of the patient into prescribed fluorescent light. Each of the photomultiplier tube 1 converts this fluorescent energy into electrical charges, after which the position calculating section 59 outputs the charges externally as position signals. In this way, the distribution of radiation energy can be displayed on the monitor for use in diagnoses.

In the brief example above, the gamma camera 50 is used as the radiation detector. However, another example of a radiation detector used in nuclear medicine diagnoses is a positron CT, known as a PET. It is obvious that a plurality of photomultiplier tube 1 according to the present invention can also be employed in this apparatus.

INDUSTRIAL APPLICABILITY

The photomultiplier tube of the present invention can be used as an optical analyzing apparatus that utilizes absorption, reflection, and polarization of specific wavelengths to analyze diverse matter. Such an apparatus has applications in a wide variety of apparatus, including medical equipment, analysis equipment, and industrial instruments.

What is claimed is:

1. A method of manufacturing a photomultiplier tube having a faceplate, a photocathode for emitting electrons in response to light incident on the faceplate, an electron multiplying section for multiplying the electrons emitted from the photocathode, an anode for outputting an output signal based on the electrons multiplied by the electron multiplying section, a stem plate for fixedly supporting the electron multiplying section and the anode with stem pins, and a side tube with the stem plate fixed on one open end and the faceplate fixed on the other open end and enclosing the electron multiplying section and the anode, the method comprising the steps of:

providing a metal side tube formed of metal and a stem plate such that at least a portion contacting the metal side tube is formed of metal;

aligning the metal side tube with the stem plate so that an outer surface of the metal side tube is flush with an edge surface of the stem plate, wherein the entirety of the outer surface of the metal side tube is substantially in parallel with an axial direction of the metal side tube when aligned; and fusing the metal side tube to the stem plate at a point of contact between the metal side tube and the stem plate by laser welding or electron beam welding to form an airtight vessel.

2. The method of manufacturing a photomultiplier tube as recited in claim 1, wherein the metal side tube is engaged with the stem plate such that only the outer surface of the metal side tube is exposed on an outer surface of the airtight vessel formed from the metal side tube and the stem plate by laser welding or electron beam welding.

3. The method of manufacturing a photomultiplier tube as recited in claim 1, wherein the metal side tube is engaged with the stem plate such that the outer surface of the metal side tube and at least a portion of an outermost edge of the stem plate are exposed on an outer surface of the airtight vessel formed from the metal side tube and the stem plate by laser welding or electron beam welding.

4. A photomultiplier tube comprising:

a faceplate;

a photocathode for emitting electrons in response to light incident on the faceplate;

an electron multiplying section, disposed inside an airtight vessel, for multiplying the electrons emitted from the photocathode; and an anode for outputting an output signal based on the electrons multiplied by the electron multiplying section, wherein the airtight vessel comprises:

a stem plate for fixedly supporting the electron multiplying section and the anode with stem pins;

a metal side tube with the stem plate fixed on one open end, and enclosing the electron multiplying section and the anode, the entirety of an outer surface of the metal side tube being substantially in parallel with an axial direction of the metal side tube; and the faceplate fixed on the other open end of the metal side tube, wherein the stem plate is welded on the one open end of the metal side tube, a top surface of the stem plate contacting a bottom end of the metal side tube such that an outer surface of the metal side tube is flush with an edge surface of the stem plate, at least a portion of the top surface of the stem plate in contact with the metal side tube being formed of metal.

5. The photomultiplier tube as recited in claim 4, wherein a cutout portion is formed in the top surface on an edge of the stem plate for supporting the bottom end of the metal side tube.

6. The photomultiplier tube as recited in claim 4, wherein the metal side tube is fusion welded to the stem plate.

7. The photomultiplier tube as recited in claim 6, wherein the fusion welding is laser welding or electron beam welding.

8. The photomultiplier tube as recited in claim 4, wherein the entirety of the stem plate is formed of metal.

9. The photomultiplier tube as recited in claim 4, wherein the stem plate comprises a metal stem support member, and a glass stem plate, the metal stem support member being in contact with the bottom end of the metal side tube extending substantially in an axial direction of the metal side tube.

10. A radiation detector comprising:

a scintillator for emitting fluorescent light in response to radiation generated from an object of analysis;

a plurality of photomultiplier tubes, each having a faceplate disposed in opposition to the scintillator, for outputting electric charges based on fluorescent light emitted from the scintillator; and a position calculating section for performing calculations on the electric charges output from the plurality of photomultiplier tubes and outputting positioning signals of radiation issued in the object of analysis, wherein each of the plurality of the photomultiplier tubes comprises:

a photocathode for emitting electrons in response to light incident on the faceplate;

an electron multiplying section, disposed inside an airtight vessel, for multiplying the electrons emitted from the photocathode; and an anode for outputting an output signal based on the electrons multiplied by the electron multiplying section, and wherein the airtight vessel comprises:

a metal stem plate for fixedly supporting the electron multiplying section and the anode with stem pins;

a metal side tube with the metal stem plate fixed on one open end, and enclosing the electron multiplying section and the anode, the entirety of an outer surface of the metal side tube being substantially in parallel with an axial direction of the metal side tube, wherein the metal stem plate is fixed by welding to the metal side tube such that an outer surface of the metal side tube is flush with an edge surface of the stem plate; and the faceplate fixed on the other open end of the metal side tube.

11. The method of claim 1, wherein the metal side tube is shaped substantially like an angular cylinder.

12. The photomultiplier tube of claim 4, wherein the metal side tube is shaped substantially like an angular cylinder.

13. The photomultiplier tube of claim 10, wherein the metal side tube is shaped substantially like an angular cylinder.

* * * * *